(12) United States Patent
Ma (10) Patent No.: US 8,761,464 B2
(45) Date of Patent: Jun. 24, 2014

(54) METHODS OF EFFICIENT AND IMPROVED PHASE-SENSITIVE MRI

(75) Inventor: Jingfei Ma, Houston, TX (US)

(73) Assignee: Boad of Regents, The University of Texas System, Austin, TX (US)

( * ) Notice: Subject to any disclaimer, the term of this patent is extended or adjusted under 35 U.S.C. 154(b) by 656 days.

(21) Appl. No.: 12/668,872

(22) PCT Filed: Jul. 10, 2008

(86) PCT No.: PCT/US2008/069662
§ 371 (c)(1),
(2), (4) Date: Jan. 26, 2010

(87) PCT Pub. No.: WO2009/012115
PCT Pub. Date: Jan. 22, 2009

(65) Prior Publication Data
US 2010/0195885 A1    Aug. 5, 2010

Related U.S. Application Data (60) Provisional application No. 60/949,537, filed on Jul. 13, 2007.

(51) Int. Cl.
*G06K 9/00* (2006.01)
*G06T 7/00* (2006.01)
*G06F 19/00* (2011.01)

(52) U.S. Cl.
CPC ............. *G06T 7/0012* (2013.01); *G06F 19/321* (2013.01)
USPC ......................................................... 382/128

(58) Field of Classification Search
CPC ........................... G06T 7/0012; G06F 19/321
USPC ......................................................... 382/128
See application file for complete search history.

(56) References Cited

U.S. PATENT DOCUMENTS

| | | | | |
|---|---|---|---|---|
| 5,321,359 A | * | 6/1994 | Schneider | 324/307 |
| 6,147,492 A | * | 11/2000 | Zhang et al. | 324/309 |
| 7,084,626 B2 | | 8/2006 | Ma et al. | |
| 7,099,499 B2 | * | 8/2006 | Blezek et al. | 382/128 |
| 2004/0064032 A1 | | 4/2004 | Ma | |
| 2005/0165296 A1 | | 7/2005 | Ma | |

OTHER PUBLICATIONS

Haase ,A., et al., 1H NMR Chemical Shift Selective (CHESS) Imaging. Physics in medicine and biology,30 (4):341-344. 1985.
Keller, P.J., et al., Multisection Fat-Water Imaging With Chemical Shift Selective Presaturation. Radiology,164 (2):539-541. 1987.
Foster, M.A., et al., Nuclear Magnetic Resonance Pulse Sequence and Discrimination of High-And Low-Fat Tissues. Magnetic resonance imaging,2(3):187-192. 1984.
Bydder, G.M. , et al., MR Imaging: Clinical Use of the Inversion Recovery Sequence. J ComputAssist. Tomogr; 9 (4):659-675. 1985.
Rofsky, N.M., et al.,. Abdominal MR Imaging With A Volumetric Interpolated Breath-Hold Examination. Radiology, 212(3):876-884. 1985.

(Continued)

*Primary Examiner* — Sheetal R Rangrej
(74) *Attorney, Agent, or Firm* — Parker Highlander PLLC (57) ABSTRACT

A single-point Dixon ("SPD") technique that can provide chemical species separation using data from a single echo with a flexible relative phase angle between the species is provided.

20 Claims, 7 Drawing Sheets

(56) References Cited

OTHER PUBLICATIONS

Dixon, W.T. Simple Proton Spectroscopic Imaging. Radiology, 153(1):189-194. 1984.

Glover, G.H. Multipoint Dixon Technique for Water and Fat Proton and Susceptibility Imaging. J Magn Reson Imaging, 1(5):521-530. 1991.

Glover, G.H., et al., Three-Point Dixon Technique for True Water/Fat Decomposition With BO Inhomogeneity Correction. Magn Reson Med, 18(2):371¬383. 1991.

Yeung, H.N., et al., Separation of True Fat and Water Images by Correcting Magnetic Field Inhomogeneity in Situ. Radiology, 159(3):783-786. 1986.

Szumowski, J., et al., Phase Unwrapping in the Three-Point Dixon Method for Fat Suppression MR Imaging. Radiology, 192(2):555-561. 1994.

Xiang, Q.S., et al., Water-Fat Imaging With Direct Phase Encoding. J Magn Reson Imaging, 7(6): 1002-1015. 1997.

Reeder, S.B., et al.,Multicoil Dixon Chemical Species Separation With an Iterative Least-Squares Estimation Method. Magn Reson Med, 51(1):35-45. 2004.

Ma, J. Breath-Hold Water and Fat Imaging Using a Dual-Echo Two-Point Dixon Technique With an Efficient and Robust Phase-Correction Algorithm. Magn Reson Med, 52(2):415-419. 2004.

Ma J, et al., Fat-Suppressed Three-Dimensional Dual Echo Dixon Technique for Contrast Agent Enhanced MRI. J Magn Reson Imaging, 23(1 ):36-41. 2006.

Ma, J., et al., A Fast Spin Echo Two-Point Dixon Technique and Its Combination With Sensitivity Encoding for Efficient T2¬weighted Imaging. Magn Reson Imaging, 23(10):977-982. 2005.

Paltiel ,Z., et al., Separate Water and Lipids Images Obtained by a Single Scan. In: Proceeedings of the fourth annual scientific meeting of the Society of Magnetic Resonance in Medicine, New York, New York, 1985. p. 172.

Patrick, J., et al., Separate Water and Lipids Images Obtained by a Single Scan. In: Proceeedings of the fourth annual scientific meeting of the Society of Magnetic Resonance in Medicine, New York, New York, 1985. p. 174.

Ahn, C.B., et al., . Spectroscopic Imaging by Quadrature Modulated Echo Time Shifting. Magn Reson Imaging, 4: 110-111. 1986.

Hajnal, J., et al., Use of Spatial Phase Distribution Models to Produce Water and Fat Only Images From Single Echo Shifted Data Sets. In: Proceedings of the third annual scientific meeting of the Society of Magnetic Resonance, 1995. p. 650.

.Xiang, Q.S. Fat Suppression With Single Quadrature Acquisition. In: Proceedings of the sixth annual scientific meeting of the ISMRM, Sydney, Australia, 1998. p. 1880.

Ma, J. Multipoint Dixon Imaging With Reduced Time and Increased Reliability. In: Proceedings of the sixth annual scientific meeting of the International Society of Magnetic Resonance in Medicine, Sydney, Australia, 1998. p. 622.

Yu, H., et al., . Single Acquisition Water-Fat Separation: Feasibility Study for Dynamic Imaging. Magnetic Resonance in Medicine : official journal of the Society of Magnetic Resonance in Medicine / Society of Magnetic Resonance in Medicine, 55(2):413¬422. 2006.

Xiang, Q.S. Improved Single Point Water-Fat Imaging With Virtual Shimming. In: Proceeedings of the ninth annual scientific meeting ofthe ISMRM, Glasgow, Scotland, 2001. p. 789.

Son, J. et al.,. Three-Dimensional T1-Weighted MR Imaging Using A One-Point Dixon Technique With Arbitrary Echo Time. In: Proceeedings of the thirteenth annual scientific meeting ofthe ISMRM, Miami, FL, 2005. p. 893.

Ma, J.,et al., . T2-Weighted Spine Imaging With A Fast Three-Point Dixon Technique: Comparison With Chemical Shift Selective Fat Suppression. J Magn Reson Imaging ,20(6):1025-1029. 2004.

Ma J. Multislice and Multicoil Phase Sensitive Inversion Recovery Imaging. Magn Reson Med, 53:904-910. 2005.

Sodickson, O.K., et al., Simultaneous Acquisition of Spatial Harmonics (SMASH): Fast Imaging With Radio Frequency Coil Arrays. Magn Reson Med, 38(4):591-603. 1997.

Pruessmann ,K.P., et al., SENSE: Sensitivity Encoding for Fast MRI. Magn Reson Med 42(5):952-962. 1999.

King, K.F., et al., SENSE Image Quality Improvement Using Matrix Regularization. In: Proceeedings of the ninth annual scientific meeting of the ISMRM, Glasgow, Scotland, 2001. p. 1771.

Foo, T.K., et al., Inversion in the Steady State: Contrast Optimization and Reduced Imaging Time With Fast Three-Dimensional Inversion¬. Recovery-Prepared ORE Pulse Sequences. Radiology, 191(1):85-90; 1994.

Ma, J. Phase-Sensitive IR Imaging and Its Application for Tissue Segmentation. In: Proceeedings of the seventh annual scientific meeting of the ISMRM, Philadelphia, Pennsylvania, 1999. p. 1652.

\* cited by examiner

METHODS OF EFFICIENT AND IMPROVED PHASE-SENSITIVE MRI

CROSS-REFERENCE TO RELATED APPLICATIONS

This application claims priority to U.S. Pat. App. Ser. No. 60/949,537 filed Jul. 13, 2007. This application is incorporated by reference herein it its entirety.

BACKGROUND OF THE INVENTION

Magnetic resonance imaging (MRI) has proven useful in the diagnosis of many diseases such as hepatic steatosis, cancer, multiple sclerosis, sports related injury, and bone marrow disorders. MRI provides unique imaging capabilities which are not attainable in any other imaging method. For example, MRI can provide detailed images of soft tissues, abnormal tissues such as tumors, and other structures which cannot be readily imaged using techniques like X-rays. Further, MRI operates without exposing patients to ionizing radiation experienced in X-rays. For these and other reasons, MRI is commonly utilized in the medical field.

In comparison to other imaging modalities, MRI is unique in that the MRI signal is represented by a complex number, rather than simply a scalar (such as X-ray attenuation in CT). The image value for each image pixel, therefore, usually includes a magnitude and a phase. Although the phase of an image pixel may carry important information and may be used in many applications such as chemical shift imaging, thermal imaging, and blood flow quantitation, it is usually discarded in the standard image reconstruction process. The underlying reason is that some unwanted error phase almost always accompanies the desired phase. Although many methods have been developed to remove the error phase, a truly reliable and automated phase correction method is still lacking.

A clinically relevant application where correction of phase errors is important is the Dixon chemical shift imaging. In MRI, the signal-emitting protons may resonate at different Larmor frequencies because they have different local molecular environments or chemical shifts. The two most distinct species found in the human body that are signal-generating for MRI are water and fat, whose Larmor or resonant frequencies are separated by about 3.5 ppm (parts per million). Typically, both water and fat will appear in an MRI image. However, in many clinical MRI applications, it is desirable to suppress signals from fat because they are usually very bright and can obscure lesions. In some clinical applications, detection and quantitation of fat may also be important. Presently, the most commonly used method for fat suppression is the chemical shift selective saturation (CHESS) method, which, despite its many advantages, is known to be intrinsically susceptible to both the radiofrequency (RF) and the magnetic field inhomogeneity. Another technique that is sometimes used for fat suppression is the short tau inversion recovery (STIR), which is based on the characteristically short T1 relaxation constant for fat, rather than on its Larmor frequency. The drawbacks of STIR include reduction in scan time efficiency and signal-to-noise ratio as well as potential alteration to the image contrast.

Several phase error correction methods have been previously published or disclosed for separating water and fat signals in MRI. In general, these methods require multiple input images with varying but specific relative water and fat phase angles. For example, in one implementation of the three-point Dixon method, three input images with a relative water and fat phase angle of 0, 180°, 360°, respectively are acquired [7-8]. In another implementation of the three-point Dixon method, three input images with a relative water and fat phase angle of 0, 90°, 180°, respectively are acquired [11]. In one implementation of the two-point Dixon method, two input images with a relative water and fat phase angle of 0 and 180°, respectively are acquired [6]. Acquisition of the multiple input images usually leads to at least doubling (in the two-point Dixon method) or tripling (in the three-point Dixon method) of the minimum total scan time. A recently disclosed phase correction method allows efficient and robust water and fat separation using two-point Dixon data when water and fat signals are 0 and 180°, respectively. When the two-point Dixon data are acquired in a dual echo with readout gradients of alternating polarity after one RF excitation, the total scan time is greatly reduced relative to that of a conventional two-point Dixon method and becomes comparable to that of a single acquisition scan. Nonetheless, two input images with specific water and fat relative phase angles (one in-phase and one 180° out of phase) are still required. Often times, the in-phase and 180° out of phase angles required in a two-point Dixon acquisition would leave out some deadtime during the TR time and cause some inflexibility in choosing the imaging parameters (e.g., the receiver bandwidth and the frequency encoding matrix size). Consequently, the true minimum scan time allowed by the system hardware and user-selected imaging parameters is not realized and the image quality is not optimized.

The referenced need for phase error corrections in MRI and shortcomings of some of the existing approaches as discussed above are not intended to be exhaustive, but rather are among many that tend to impair the effectiveness of previously known techniques concerning image data acquisition and image reconstruction; however, those mentioned here are sufficient to demonstrate that the methodologies appearing in the art have not been satisfactory and that a significant need exists for the techniques described and claimed in this disclosure.

DETAILED DESCRIPTION OF THE DRAWINGS

Some specific example embodiments of the disclosure may be understood by referring, in part, to the following description and the accompanying drawings.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION

The present disclosure relates to methods for improved-phase sensitive MRI. More particularly, the present disclosure relates to a single-point Dixon ("SPD") technique that can provide chemical species separation using data from a single echo with a flexible relative phase angle between the species. In certain embodiments, the SPD technique may provide one or more of a water-only image and a fat-only image from a single echo when water and fat are placed at a relative angle the is substantially out of phase. The SPD technique may provide one or more of a silicone-only image and a tissue-only (water+fat) image from a single echo data when water and fat are placed at a relative angle that is substantially in-phase.

The present invention includes a method and apparatus for phase sensitive magnetic resonance imaging using a novel SPD technique that can provide robust water and fat separation from a single echo data with a flexible water and fat relative phase angle, or robust silicone and tissue (water+fat) separation when water and fat are placed at a relative phase angle that is substantially in-phase. Son, J., et al., *Three-Dimensional T1-Weighted MR Imaging Using a One-Point Dixon Technique With Arbitrary Echo Time*, In: Proceedings of the Thirteenth Annual Scientific Meeting of the International Society of Magnetic Resonance in Medicine, Miami, Fla., 2005, p 893. The technique is based on a fully automated region growing algorithm for phase error correction and is compatible with phased array coil acquisition and partially parallel imaging. By eliminating the need for the preparatory pulses used conventionally for fat suppression and relaxing the constraint for a specific echo time (to achieve a specific water/fat relative phase angle), the technique may realize the maximum scan time efficiency when it is implemented with the three-dimensional (3D) or two-dimensional (2D) fast gradient echo pulse sequence.

The applicability of the novel SPD technique disclosed herein to data acquired with a flexible echo time has very tangible advantages in its application. In many modern fast pulse sequences, the play-out of the gradient and RF pulses as well as the data acquisition window is packed as tightly as possible (subject to the imaging principles) to achieve the maximum scan time efficiency and optimal image quality. Such timing requirement of a pulse sequence often does not coincide fortuitously with the requirement for the specific water/fat phase angles by a typical Dixon implementation. In the fast gradient echo pulse sequence, for example, the TR and TE used are often below the minimum values that are allowed by the scanner hardware configuration and the user-selectable imaging parameters. The 90° water/fat relative phase angle as required in a previously-proposed quadrature sampling, for example, would correspond to a TE of 1.28 ms at 1.5 Tesla. Since such a short TE is often not attainable for many practical imaging parameters, the TE (and TR) values would have to be increased by at least 2 ms to reach the next TE required for quadrature sampling. The resulting increase in TR (from a typical value of 4-6 ms) would lead to a significant increase in scan time and the resulting increase in TE would lead to more signal decay and image blurring.

Figure 1:
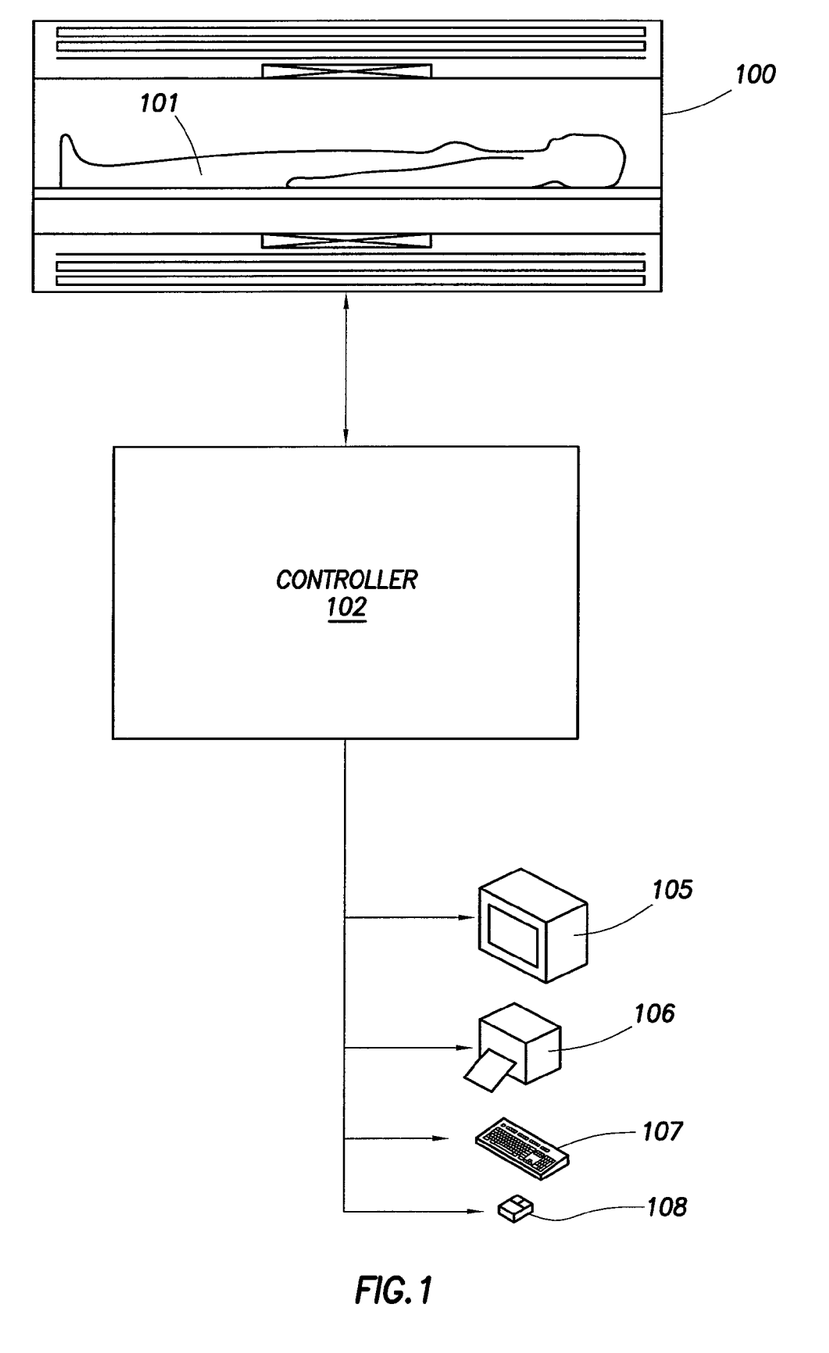
FIG. 1 illustrates a magnetic resonance imaging system in accordance with an embodiment of the present disclosure.

In FIG. 1, an MRI apparatus, in accordance with an embodiment of the present invention, is presented. The MRI apparatus includes a scanner 100, a controller 102, output devices such as a display screen 103, an output printing device 104, and input devices such as a keyboard 105 and a mouse 106.

Figure 2:
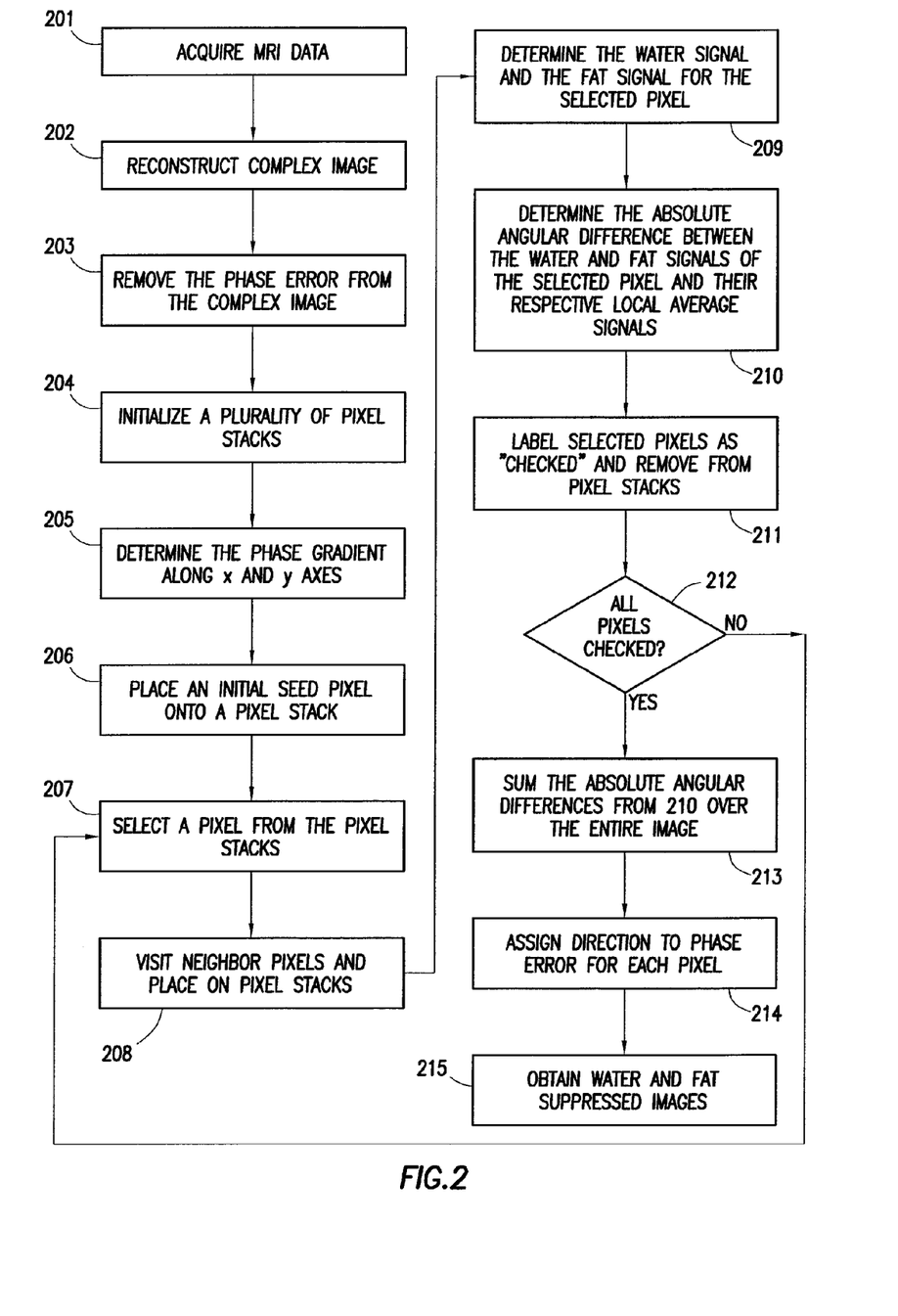
FIG. 2 is a flowchart showing steps of a method in accordance with an embodiment of the present disclosure.

To obtain an image, a patient 101 is placed inside a scanner 100, which receives instructions about generating image data from the controller 102. The controller 102 obtains the data, processes the data to obtain desired image(s), and outputs the final image(s) to an output device of choice, such as a display monitor 103 or a printer 104. One of the various methods that may be utilized by the controller 102 is shown in FIG. 2. The controller 102 may also receive user input from input devices such as a keyboard 105 or a mouse 106, which dictates the type of images that are taken of the patient 101.

A flowchart showing the steps of an embodiment of the present invention is given in FIG. 2. In step 201, MRI image data is obtained from a subject after the scanning process. A single echo data with a flexible water and fat relative phase angle may be used. A variety of echo times ("TE") may be utilized to acquire the image. As such, the advantages of the single-echo acquisition may minimize scan time and patient motion related artifacts, allowing for a single breath hold examination of the entire abdomen. Further, the complete elimination of patient respiratory motion or slice misregistsration artifacts may be obtained utilizing the efficient data acquisition method.

Image Acquisition

Steps 202 and 203 of FIG. 2 comprise an image reconstruction scheme. In step 202, the image may first be reconstructed using a fast Fourier transform. Assuming that the object to be imaged contains only two chemical species (i.e., water and fat) with each being represented by a single spectral peak, the complex image after the Fourier transform of the k-space data for a given slice (of index m) and a given receiver coil (of index n) can be written in general as follows:

$$S_{m,n}(x,y)=[W_{m,n}(x,y)+e^{i\theta}F_{m,n}(x,y)]e^{i\phi_{m,n}(x,y)} \qquad [1]$$

Glover, G. H., *Multipoint Dixon Technique For Water and Fat Proton and Susceptibility Imaging*, J Magn Reson Imaging, 1991, 1(5):521-530; Ma, J., et al., *T2-Weighted Spine Imaging With a Fast Three-Point Dixon Technique: Comparison With Chemical Shift Selective Fat Suppression*, J Magn Reson Imaging, 2004, 20(6):1025-1029.

In Eq. [1], x and y represent the spatial coordinates of an image pixel. W and F are the water and fat signal amplitudes weighted by the relaxation and receiver coil sensitivity. $\phi$ is the phase error that may include the contribution from the magnetic field inhomogeneity, eddy currents, and those that arise from the different RF penetration, signal delay in the receiver chains, and the data acquisition timing inaccuracy.

Therefore, $\phi$ is in general a function of (x,y) and (m,n). $\theta$ is the phase shift due exclusively to the chemical shift and therefore is dependent only on the echo time for a given field strength.

Figure 3:
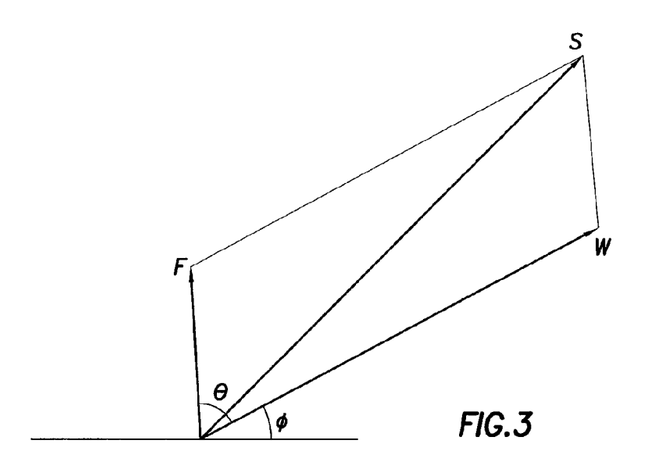
FIG. 3 shows a vector representation of the complex signal S as given in Eq. [1] for a given pixel with two spectral component, water (W) and fat (F).

FIG. 3 displays a vector representation of the signal by Eq. [1]. For a given acquisition, $\theta$ is a known constant. When $\phi$ is not zero and unknown, W and F in general cannot be determined from S. However, $\phi$ is known to be smoothly varying from pixel to pixel (an assumption that serves as the basis for all Dixon techniques). Under a further assumption that an image pixel with signals is either water-dominant or fat-dominant, the direction of S is expected to be slowly changing within a region of either water-dominance or of fat-dominance. Across boundaries between water-dominant and fat-dominant regions, the direction of S is expected to change by $\theta$. The present disclosure uses this simple observation to automatically determine the direction of the phase errors (as represented by $e^{i\phi_{m,n}(x,y)}$) and remove it from Eq. [1].

Thus in step 203, the water and fat signal amplitudes can simply be derived as:

$$F_{m,n}(x,y) = \text{Im}(S'_{m,n}(x,y))/\sin(\theta) \quad [2]$$

$$W_{m,n}(x,y) = \text{Re}(S'_{m,n}(x,y)) - F_{m,n}(x,y)\cos(\theta) \quad [3]$$

where Im( . . . ) and Re( . . . ) represent the operation of taking the imaginary and real parts and S', which is the signal in Eq. [1] after the phase error correction, or:

$$S'_{m,n}(x,y) = S_{m,n}(x,y) e^{-i\phi_{m,n}(x,y)} \quad [4]$$

Determination of Phase Error

In steps 204-214, a phase correction algorithm may be implemented to determine the phase error vector $e^{i\phi_{m,n}(x,y)}$. For each complex image $S_{m,n(x,y)}$, we used a region growing algorithm as described below to determine $e^{i\phi_{m,n}(x,y)}$. The algorithm implemented in the present invention was modified and generalized from a region growing process developed for the two-point Dixon and phase sensitive inversion recovery techniques, which is disclosed in U.S. Patent Publication No. 2005/0165296 the entirety of which is herein incorporated by reference. Ma, J., *Breath-Hold Water and Fat Imaging Using a Dual-Echo Two-Point Dixon Technique With an Efficient and Robust Phase-Correction Algorithm*, Magn Reson Med, 2004, 52(2):415-419; Ma, J., et al., *Fat-Suppressed Three-Dimensional Dual Echo Dixon Technique For Contrast Agent Enhanced MRI*, J Magn Reson Imaging, 2006, 23(1):36-41; Ma, J., *Multislice and Multicoil Phase Sensitive Inversion Recovery Imaging, Magn Reson Med*, 2005, 53:904-910.

Before initiating and performing the region-growing process, a few preliminary steps may be performed prior to the actual region growing. In step 204, a series of pixel stacks (that may each be represented conveniently by a one-dimensional array) may be established. These pixel stacks are sequentially ordered and initially all empty. Each pixel stack may be used to cover an incremental segment of the total angular range for $(DX)_{m,n}$ and $(DY)_{m,n}$ (see step 205 below), which ranges between 0 to $\pi$. In one embodiment, the pixel stacks may initially be all empty. The total number of pixel stacks may vary, but in general, covers the angular range with sufficient resolution. For example, 18 pixel stacks would allow each pixel stack to cover 10°, which may be sufficient in many applications.

Before initiating and performing the region-growing process, a phase gradient map along the x-direction between neighboring pixels is calculated in step 205 as follows:

$$(DX)_{m,n}(x,y) = \left| \arg\left( S_{m,n}^{(\frac{2\pi}{\theta})}(x,y) \cdot S_{m,n}^{(\frac{2\pi}{\theta})^*}(x+1,y) \right) \right| \quad [5]$$

in which ||, arg( . . . ), and * represent the magnitude, phase argument, and complex conjugate operations, respectively. In a similar fashion, $(DY)_{m,n}$, a phase gradient map along the y-axis between neighboring pixels, is also calculated. Because of the magnitude operation, both $(DX)_{m,n}$ and $(DY)_{m,n}$ are within the range of 0° to 180°. Taking the $2\pi/\theta$-th power of $S_{m,n}$ in Eq. [5] removes the possible abrupt phase changes across the water/fat boundaries. As a result, $DX_{m,n}$ and $DY_{m,n}$ are expected to be spatially smooth. Together with the pixel stacks created above, $DX_{m,n}$ and $DY_{m,n}$ may be used to guide the sequence of the region growing, as detailed below in steps 206-212. To minimize the impact of noise and local phase fluctuations, the argument within the arg( . . . ) operation (which is naturally weighted approximately by the square of the signals) in Eq. [5] may optionally be low-pass filtered (for example, with a 3×3 kernel).

In step 206, the region growing process is initiated by selecting an initial seed pixel and place it onto one of the pixel stacks. Although its selection is also quite flexible, the pixel with the smallest $DX_{m,n}$ (or $DY_{m,n}$) value may be chosen as the initial seed pixel. Statistically speaking, such a pixel is more likely to be from a region with high SNR and small phase variations. However, the initial seed pixel thus selected could be either a water-dominant pixel or a fat-dominant pixel. In either case, this pixel will be labeled as having been "checked" after its selection.

The actual region growing is a looped two-step process. In step 207 a pixel is selected from a pixel stack that has the lowest stack order and is not empty. At the beginning, the initial seed pixel will be selected because it is the only pixel on the pixel stacks. In step 208, the region growing then "visits" each of its four nearest neighbor pixels and places them onto one of the pixel stacks. Which pixel stack the nearest neighbor pixels will be placed onto is determined by each pixel's $DX_{m,n}$ or $DY_{m,n}$ value with respect to the pixel that is under consideration. If the $DX_{m,n}$ or $DY_{m,n}$ value is small, the nearest neighbor pixel being visited will be placed on a pixel stack with a low stack order. Conversely, if the $DX_{m,n}$ or $DY_{m,n}$ value is large, the nearest neighbor pixel being visited will be placed on a pixel stack with a high stack order. Since the maximum angular range of $DX_{m,n}$ and $DY_{m,n}$ is 180° and a total of 18 pixel stacks are used, each pixel stack covers an angular difference of 10°. Only pixels that have not been marked "checked" will be visited (see below). Note that during the region growing process, an image pixel may be "visited" up to a maximum of four times and placed onto up to a maximum of four different pixel stacks.

In the second phase of the region growing, the direction of $e^{i\phi_{m,n}(x,y)}$ for the pixel that has been selected from the pixel stack for consideration is determined. For this purpose, the values of $\overline{S_{m,n}^w(x,y)}$ and of $\overline{S_{m,n}^f(x,y)}$ for the pixel that is under consideration are calculated as follows:

$$\overline{S_{m,n}^w(x,y)} = \sum_{(x,y)} S_{m,n}^w(x,y) \cdot Chk_{m,n}(x,y) \quad [6]$$

$$\overline{S_{m,n}^f(x,y)} = \sum_{(x,y)} S_{m,n}^f(x,y) \cdot Chk_{m,n}(x,y) \quad [7]$$

where $Chk_{m,n}(x,y)$ is a mask matrix whose value is 1 for the pixels that have been labeled as "checked" and 0 for the pixels that have not been "checked". The summation is performed over a local region conveniently defined by a boxcar centered at the pixel under consideration. Therefore, the directions of $\overline{S_{m,n}^{w}(x,y)}$ and of $\overline{S_{m,n}^{f}(x,y)}$ can serve as the projected directions of $S_{m,n}^{w}(x,y)$ and $S_{m,n}^{f}(x,y)$, respectively. The size of the boxcar may be fixed (for example, 18×18) or adaptively varied between a certain range (for example, 12×12 to 24×24) according to the pixel's $DX_{m,n}$ or $DY_{m,n}$ values. $S_{m,n}^{w}(x,y)$ and $S_{m,n}^{f}(x,y)$ appear identical in Eqs. [6-7] but are actually used for tracking two different possible situations when the initial seed pixel is water-dominant and fat-dominant, respectively. Both $S_{m,n}^{w}(x,y)$ and $S_{m,n}^{f}(x,y)$ take the value of $S_{m,n}(x,y)$ for the initial seed pixel. However, for all other pixels, the $S_{m,n}^{w}(x,y)$ and $S_{m,n}^{f}(x,y)$ values will be determined on the basis of the angular differences between $\overline{S_{m,n}^{w}(x,y)}$ and of $S_{m,n}(x,y)$ as well as between $\overline{S_{m,n}^{f}(x,y)}$ and $S_{m,n}(x,y)$ that are calculated in step 209 as follows:

$$\psi^{w}(x,y)=\angle(S_{m,n}(x,y),\overline{S_{m,n}^{w}(x,y)}) \quad [8]$$

$$\psi^{f}(x,y)=\angle(S_{m,n}(x,y),\overline{S_{m,n}^{f}(x,y)}) \quad [9]$$

Figures 4A, 4B:
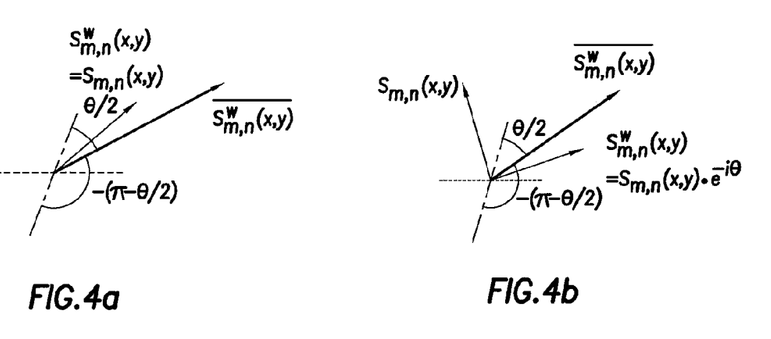
FIGS. 4a-4d show the phase error correction for a given pixel as dependent on whether the region growing started from a water-dominant pixel (FIGS. 4a-4b) or from a fat-dominant pixel (FIGS. 4c-4d)
Figure 4C:
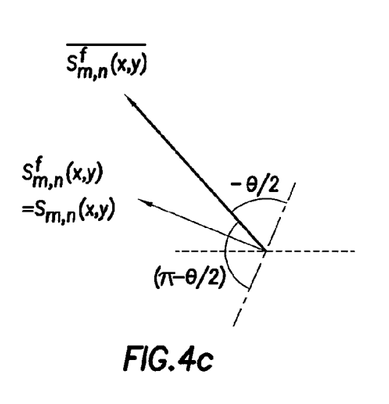
Figure 4D:
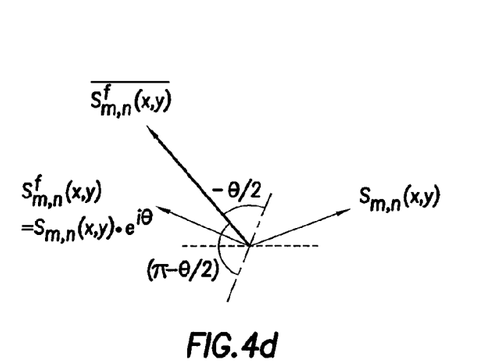

As illustrated in FIGS. 4a-4b, $S_{m,n}^{w}(x,y)$ takes the value of $S_{m,n}(x,y)$ when $\psi^{w}(x,y)$ is less than $\theta/2$ and greater than $-(\pi-\theta/2)$. When $\psi^{w}(x,y)$ is greater than $\theta/2$ or less than $-(\pi-\theta/2)$, $S_{m,n}^{w}(x,y)$ takes the value of $S_{m,n}(x,y) \cdot e^{-il}$. Similarly as in FIGS. 4c-4d, $S_{m,n}^{f}(x,y)$ takes the value of $S_{m,n}(x,y)$ when $\psi^{f}(x,y)$ is greater than $-\theta/2$ and less than $(\pi-\theta/2)$. When $\psi^{f}(x,y)$ is less than $-\theta/2$ or greater than $(\pi-\theta/2)$, $S_{m,n}^{f}(x,y)$ takes the value of $S_{m,n}(x,y) \cdot e^{il}$. Separately, in step 210 the absolute angular difference between $S_{m,n}^{w}(x,y)$ and $\overline{S_{m,n}^{w}(x,y)}$ as well as that between $S_{m,n}^{f}(x,y)$ and $\overline{S_{m,n}^{f}(x,y)}$ will be calculated and stored for the pixel:

$$\delta^{w}(x,y)=|\angle(S_{m,n}^{w}(x,y),\overline{S_{m,n}^{w}(x,y)})| \quad [10]$$

$$\delta^{f}(x,y)=|\angle(S_{m,n}^{f}(x,y),\overline{S_{m,n}^{f}(x,y)})| \quad [11]$$

After $S_{m,n}^{w}(x,y)$, $S_{m,n}^{f}(x,y)$, $\delta^{w}(x,y)$ and $\delta^{f}(x,y)$ are determined, the pixel that is under consideration will be labeled as having been "checked" and will be removed from the pixel stack in step 211. Afterwards, a new pixel will be selected from the pixel stacks, and the two-phase region growing process will be repeated until all the pixels in the image have been marked as "checked" according to step 212.

After the completion of the region growing, the pixel values of $\delta^{w}(x,y)$ and $\delta^{f}(x,y)$ are both summed up over the entire image in step 213. If the initial seed pixel is water-dominant, we expect that the summed value of $\delta^{w}(x,y)$ is less than that of $\delta^{f}(x,y)$. Conversely, if the initial seed pixel is fat-dominant, the summed value of $\delta^{w}(x,y)$ is greater than that of $\delta^{f}(x,y)$. Therefore, either $S_{m,n}^{w}(x,y)$ or $S_{m,n}^{f}(x,y) \cdot e^{i\theta}$ is assigned to a new matrix $S_{m,n}''(x,y)$, depending on whether the summed value of $\delta^{w}(x,y)$ is less or greater than the summed value of $\delta^{f}(x,y)$.

Theoretically, the direction of $S_{m,n}''(x,y)$ should be parallel to the direction of $e^{i\Phi_{m,n}(x,y)}$ for all the pixels. However, local and isolated inconsistency may occur in certain situations. For example, when the initial seed pixel happens to be from a noisy region (an unlikely but nonetheless possible scenario), the determination of $S_{m,n}^{w}(x,y)$ or $S_{m,n}^{f}(x,y)$ can be unreliable before the region growing reaches a region of good SNR and becomes stable. To rectify such situations, a local filtering may be applied in step 214 by first calculating for each pixel the angular difference between $S_{m,n}''(x,y)$ and its local average (e.g., over a 18×18 boxcar). If the angular difference is less than $\theta/2$ and greater than $-(\pi-\theta/2)$, $S_{m,n}''(x,y)$ keeps its original value. When the angular difference is greater than $\theta/2$ or less than $-(\pi-\theta/2)$, $S_{m,n}''(x,y)$ is replaced with the value of $S_{m,n}''(x,y) \cdot e^{il}$.

Lastly, $S_{m,n}''(x,y)$ may be smoothed with a low-pass filtering (for example, a 18×18 boxcar) before its direction is assigned to $e^{i\Phi_{m,n}(x,y)}$ in step 214 and used in Eqs. [2-3] to obtain fat-suppressed and water-suppressed images in step 215. Because of the amplitude weighting in $S_{m,n}''(x,y)$, the low-pass filtering may reduce greatly the impact of noise on the phase errors. It may also have the added advantage of relaxing to some extent the assumption that a pixel with signals is either water-dominant or fat-dominant. As long as they are localized, pixels with a mixture of water and fat (for example, along water/fat boundaries) are expected to have lower signal amplitudes than neighboring pixels of either water or fat dominance. As a result, the low-pass filtering may effectively reduce the impact of the deviation between the directions of the actually measured signal $S_{m,n}(x,y)$ and the sought-after $e^{i\Phi_{m,n}(x,y)}$.

Large areas of mixed water and fat may be present in some situations (for example, in the liver of patients with severe hepatosteatosis). Unlike pixels along the boundaries of water and fat-dominant regions that may contain both water and fat due to partial voluming, the phase error vectors for large areas of mixed water and fat can not be easily low-pass filtered and thus their accurate determination may be problematic. When image pixels contain arbitrary amounts of water and fat and phase errors are unknown, separation of water and fat from a single echo data is in general not possible. Nonetheless, the technique of the present disclosure should still be very valuable because many anatomic regions of interest are known to be of only tissues of either water or fat dominance. Furthermore, only qualitative (rather than accurate and quantitative) fat suppression is needed in many clinical applications.

Combination of Images from Different Receiver Coils

When the water and fat signals are sampled at an asymmetric relative phase angle, the water-suppressed and fat-suppressed images can be directly identified on the basis of the phase angle relationship. However, when the water and fat relative phase angle is close to 180°, distinguishing between water and fat is not possible from their phase relationship alone. Xiang, Q. S., et al., *Water-Fat Imaging With Direct Phase Encoding*, J Magn Reson Imaging, 1997, 7(6):1002-1015. As a result, automatic and consistent combination of the water-suppressed and fat-suppressed images from different receiver coils is problematic. Thus in certain embodiments, the method embodied in FIG. 2 may further comprise the following. Specifically, the following four coil-coil correlation indices for two neighboring coils after the water and fat separation may be calculated:

$$\zeta^{(w,w)}=\Sigma W_{m,n} \cdot W_{m,n+1} \quad [12]$$

$$\zeta^{(f,f)}=\Sigma F_{m,n} \cdot F_{m,n+1} \quad [13]$$

$$\zeta^{(w,f)}=\Sigma W_{m,n} \cdot F_{m,n+1} \quad [14]$$

$$\zeta^{(f,w)}=\Sigma F_{m,n} \cdot W_{m,n+1} \quad [15]$$

where the summation is performed over all the pixels. Since the water-suppressed or fat-suppressed images of a given slice from different receiver coils should theoretically differ only by the different coil sensitivity maps, the water and fat assignment for the two coils are consistent if either $\zeta^{(w,w)}$ or $\zeta^{(f,f)}$ has the maximum value among the four quantities calculated in Eqs. [12-15]. If this condition is not met, the water and fat assignment for one of the coils will be interchanged before the images from the two different coils are combined.

Such procedure is applied to the images from all receiver coils before the final combined images (using the standard sum-of-squares method) are generated.

Partially Parallel Imaging

For data acquired with partially parallel imaging, a complex full-FOV image is first generated for each slice after using the coil sensitivity maps to remove spatial aliasing. Sodickson, D. K., et al., *Simultaneous Acquisition of Spatial Harmonics (SMASH): Fast Imaging With Radiofrequency Coil Arrays*, Magn Reson Med, 1997, 38(4):591-603; Pruessmann, K. P., et al., *SENSE: Sensitivity Encoding For Fast MRI*, Magn Reson Med, 1999, 42(5):952-962. Because the unfolding matrix used in any partially parallel imaging processing does not alter the relative phase between water and fat signals, the functional form of the signals as expressed in Eq. [1] is preserved. Ma, J., et al., *A Fast Spin Echo Two-Point Dixon Technique and Its Combination With Sensitivity Encoding For Efficient T2-Weighted Imaging*, Magn Reson Imaging, 2005, 23(10):977-982. As a result, the same phase correction algorithm may be applied for water and fat separation. Furthermore, the partially parallel imaging processing obviates the need for combination of the images from different coils by using the criteria in Eqs. [12-15].

It should be understood that although the disclosure is described in the context of separating water and fat using data from a single echo acquisition with a very flexible echo time, the present invention can also be used in other applications. For example, the present invention can be used to generate silicone-only images for detection of silicone implant ruptures. In such an application, there are usually three separate and distinct chemical species within the imaging volume (for example, the breast). These three chemical species are water, fat, and silicone. The resonance frequencies of these three chemical species are approximately 0, 3.5 ppm, and 4.7 ppm respectively. In such a situation, the echo time or echo shift of the single echo acquisition can be chosen so that the water and fat signals are substantially in-phase (for example, 360° in-phase). At the same echo time, the silicone signal will be at approximately 483° (or equivalently 123°) relative to the water or fat signals. Since water and fat signals are in-phase, the present invention can be applied to separate silicone from the water and fat. As a result, a silicone-only image (in which both water and fat signals are suppressed) and a combined water and fat image (in which the silicone signals are suppressed) can be generated for each slice.

EXAMPLES

All experiments in the following examples 1-4 were performed on GE 1.5-Tesla whole body scanners that operate under the 12× EXCITE platform (GE Healthcare Technologies, Milwaukee, Wis.). Data were collected using two state-of-the-art fast 3D spoil gradient echo pulse sequences that are available as commercial products on the scanners (LAVA, or Liver Acquisition with Volume Acceleration for abdomen imaging, and VIBRANT, or Volume Image Breast Assessment for breast imaging). Both sequences can be run with and without partially parallel imaging (ASSET), and with and without the optional spectral inversion preparatory pulses for FS (SPECIAL). Pruessmann, K. P., et al., *SENSE: Sensitivity Encoding For Fast MRI*, Magn Reson Med, 1999, 42(5):952-962; King, K. F., et al., *SENSE Image Quality Improvement Using Matrix Regularization*, In: Proceedings of the Ninth Annual Scientific Meeting of the International Society of Magnetic Resonance in Medicine, Glasgow, Scotland, 2001, p 1771; Foo, T. K., et al., *Inversion in the Steady State: Contrast Optimization and Reduced Imaging Time With Fast Three-Dimensional Inversion-Recovery-Prepared GRE Pulse Sequences*, Radiology, 1994, 191(1):85-90. The SPD image reconstruction algorithm was implemented in Matlab (The MathWorks, Natick, Mass.) and used as its input the raw data files that were saved on the scanners. For data acquired with partially parallel imaging, the image unaliasing was achieved by using the software that is available as a commercial product on the scanner. Other than the raw data file names, the Matlab image reconstruction algorithm was fully automatic and required no other user input. All patient studies were conducted with the approval by the University of Texas M. D. Anderson Cancer Center Institutional Review Committee.

For phantom evaluation, a water/fat bottle consisting of approximately half soybean oil and half distilled water (doped with 0.75 mM of Magnevist contrast agent) was prepared and used for imaging. The T1/T2 for the Magnevist solution and the soybean oil were measured to be 213/144 ms and 237/50 ms, respectively. The phantom was placed in an eight-channel phased array head coil and imaged with the LAVA pulse sequence with and without the SPECIAL pulses for FS. The scanning protocol used was as follows: repetition time (TR)=minimum, acquisition matrix=256×192, receiver bandwidth=83.3±kHz, FOV=34 cm, excitation angle=12°, and coverage of 28 slices of 6 mm slice thickness. The echo time was varied manually from 1.4 ms (the minimum allowed by the system for the protocol chosen) to 2.5 ms. For the silicone implant imaging, a silicone breast implant was placed next to a water and fat phantom to evaluate the technique's capability to separate silicone from the water and fat.

Example 1

Water/Fat Phantom Images

Figure 5:
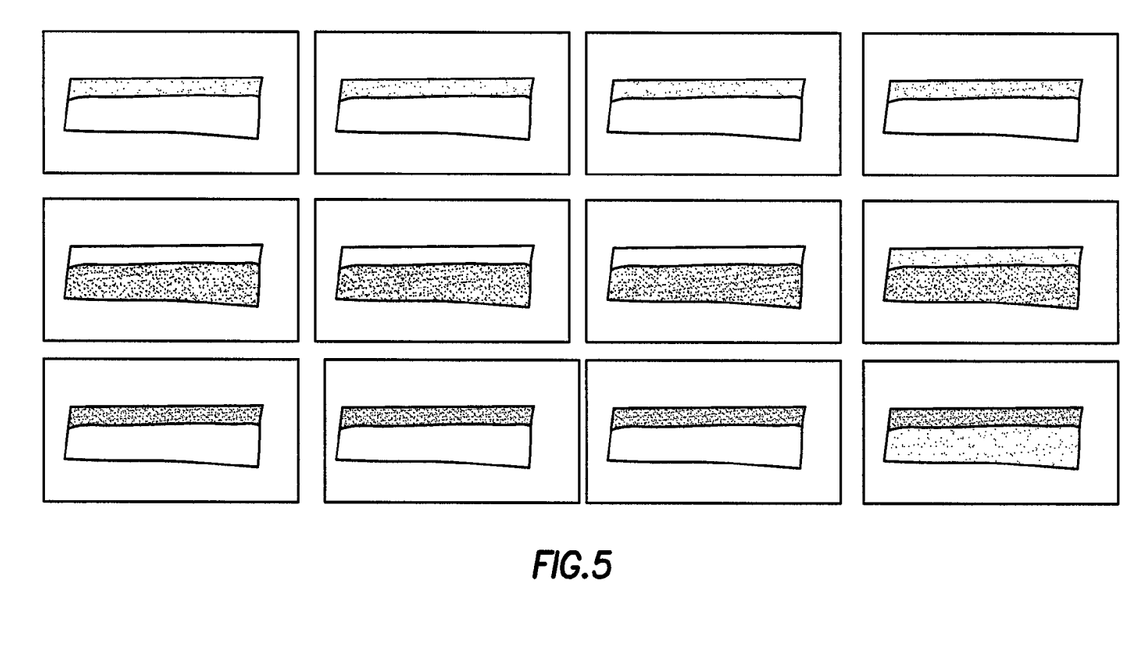
FIG. 5 shows regular images (top row), water-suppressed images (middle row), and fat-suppressed images of a water/fat phantom at four different echo times (1.42 ms, 1.62 ms, 1.82 ms and 2.02 ms, from left to right).
Figure 6:
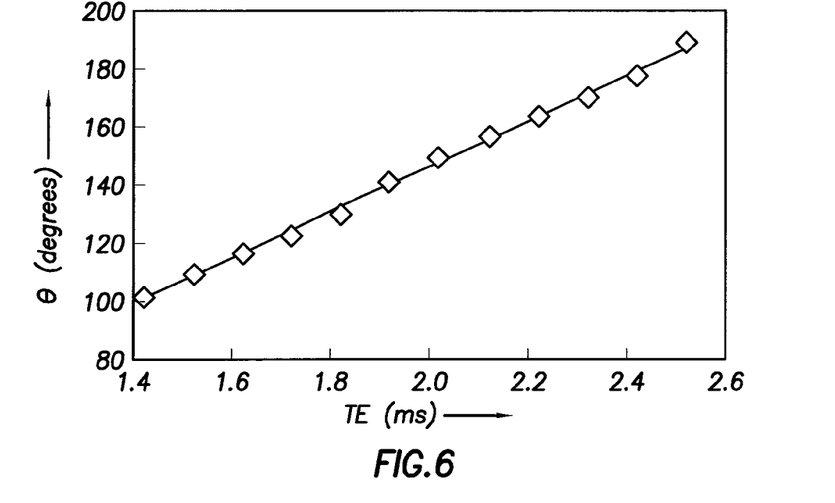
FIG. 6 depicts the relative water/fat phase angle ($\theta$) as a function of the echo times (TE), as determined from the water/fat phantom.

The top row of FIG. 5 shows the regular images of a selected slice of the phantom at four different echo times (1.42 ms, 1.62 ms, 1.82 ms and 2.02 ms). FIG. 6 displays the relative phase angle between water and fat (as determined from the phase discontinuity across the water and fat boundaries) as a function of the echo times. A linear fit of the data yields the following equation:

$$\theta(degree)=78.4 \cdot TE(ms)-10.6 \qquad [16]$$

For both the water/fat phantom and the in vivo experiments below, Eq. [16] was used to determine θ for a given TE. For the four images shown in FIG. 5 (top row), the relative water and fat phase angles are therefore 100.7°, 116.4°, 132.1° and 147.8°, respectively. The second row and the third row display the water-suppressed and fat-suppressed images that correspond to the images in the top row. As illustrated, good image quality and clean water/fat separation were achieved in all different TEs.

Example 2

In Vivo Images

Figure 7:
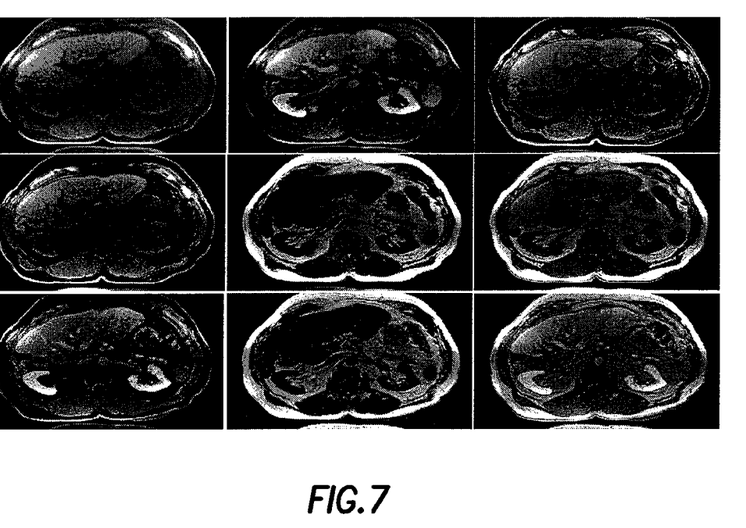
FIG. 7 shows a comparison of abdomen LAVA images with SPECIAL for fat suppression (FS) and the single point Dixon (SPD) images of a patient with colon cancer, both pre and post contrast agent administration.

FIGS. 7a and 7b show one of the 3D abdomen LAVA images with SPECIAL for FS before and after the contrast agent administration of a colon cancer patient with liver metastases. The images were acquired with an 8-channel torso phased-array coil and the imaging parameters used were as follows: TR/TE=3.5/1.7 ms, acquisition matrix=320× 160×50 (zipped to 100 slices), FOV=40×28 cm, slice thickness=5 mm (zipped to 2.5 mm), receiver bandwidth=±83.33 kHz, and total scan time=19 seconds. FIGS. 7d-7f show the SPD fat-suppressed and water-suppressed images, as well as the original LAVA image without SPECIAL for FS of the same slice before the contrast agent administration. FIGS. 7g-7i show the three corresponding SPD images after the contrast agent administration. The SPD images both before and after the contrast agent administration were acquired with the identical scan parameters as the LAVA images with SPECIAL for FS, except that the scan time was reduced to 14 seconds due to the removal of the SPECIAL pulses. According to Eq. [16], the relative phase angle between water and fat for the acquisition was 122° at the TE of 1.7 ms. During the generation of the SPD images, the two values by Eqs. [10-11] (averaged over all image pixels) were found to be consistently 20% apart for each of the eight images for a receiver coil. Thus, the two region growing (one assuming the initial seed is a water-dominant pixel and another assuming that the initial seed is a fat-dominant pixel) can be reliably differentiated. Likewise, the maximum value of $\zeta^{(w,w)}$ and $\zeta^{(f,f)}$ (as given in Eqs. [12-13]) was consistently larger by three folds than the maximum value of $\zeta^{(w,f)}$ and $\zeta^{(f,w)}$ as given in Eqs. [24-15]), thus ensuring the correct water/fat identification for combination of the images from two different coils.

FIG. 7c shows another SPD fat-suppressed image of the same slice before the contrast agent administration. The image in FIG. 7c was acquired with the same scan parameters as for the images in FIGS. 5d-5f except with a change of the receiver bandwidth from ±83.33 kHz to ±62.6 kHz. As a result, TE became 2.0 ms, which corresponds to a water/fat relative phase angle of 145°. Comparison of the images in FIGS. 5c and 5d demonstrate that the SPD technique provided consistent water and fat separation at the two different relative water/fat phase angles. Furthermore, comparison of the SPD images with the LAVA images with SPECIAL for FS demonstrate that the SPD image can be acquired in a substantially shorter scan time and with better image quality (both before and after contrast agent injection) than the LAVA images with SPECIAL for FS.

Example 3

In Vivo Images

Figure 8:
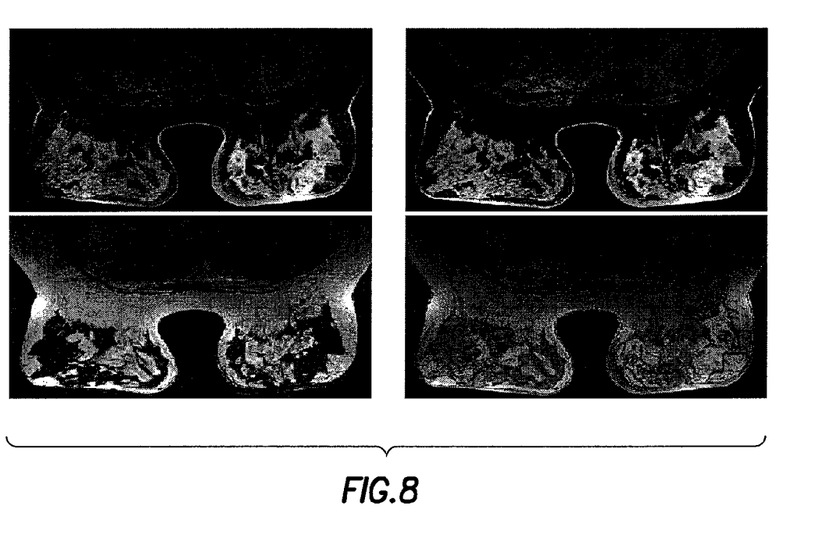
FIG. 8 shows a comparison of post-contrast bilateral VIBRANT breast images with SPECIAL for FS and the SPD images of a patient with breast cancer.

FIG. 8a shows one of the 3D bilateral breast VIBRANT images with SPECIAL for FS and partially parallel imaging after the contrast agent administration of a patient with breast cancer. The imaging parameters used were as follows: TR/TE=6.2/3.0 ms, acquisition matrix=512×352×74 (zipped to 148 slices), FOV=37×37 cm, slice thickness=3 mm (zipped to 1.5 mm), receiver bandwidth=±62.5 kHz, acceleration factor=2, and total scan time=1:24 minutes. FIGS. 8b-8d shows the SPD fat-suppressed and water-suppressed images, as well as the original VIBRANT image with partially parallel image and without SPECIAL for FS of the same slice after the contrast agent administration. The SPD images were acquired with the identical scan parameters as the VIBRANT images with SPECIAL for FS, except that the scan time was reduced to 1:01 minutes due to the elimination of the SPECIAL pulses. With a TE of 3.0 ms, the relative phase angle between water and fat for the acquisition was 227° according to Eq. [16]. As for the abdomen images, the SPD technique provided good water and fat separation with a substantial time saving when compared to the VIBRANT with SPECIAL for FS.

Example 4

Water/Fat Phantom Images

Figure 9:
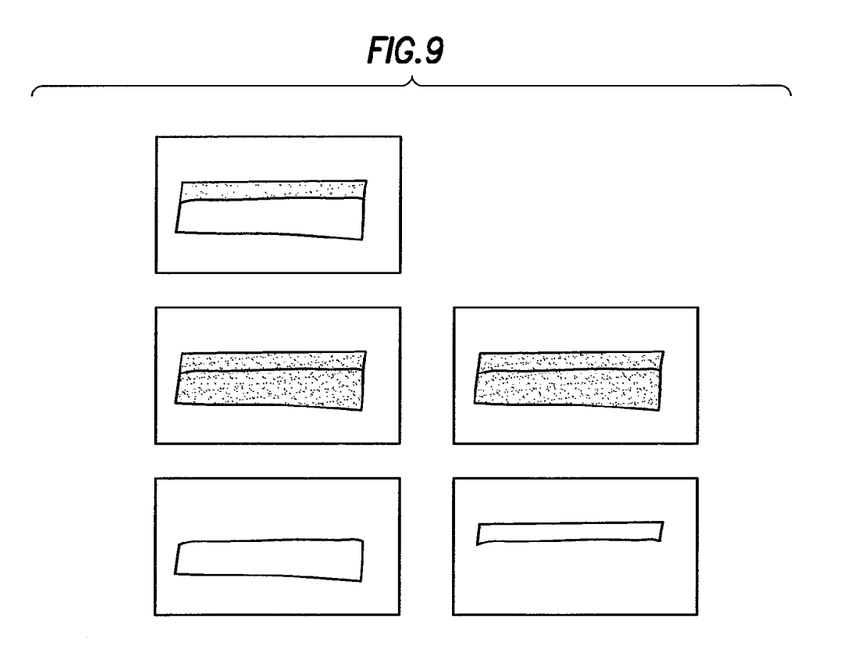
FIG. 9 shows the SPD phantom images at a TE of 2.42 ms (which corresponds to a relative water and fat phase angle of 179.2°).

According to Eqs. [2-3], difficulties may arise for water and fat separation with the disclosed SPD technique when the water and fat signals are either in-phase or 180° opposed-phase. The presence of the image noise and artifacts usually may further render the phase angles that fall within approximately ±30° of these in-phase and 180° opposed-phase values non-usable. Practically, the restriction for the in-phase values is usually a non-issue for clinical imaging using the fast gradient echo pulse sequence because the minimum TE almost always corresponds to a phase angle that is well between 90° and 270° (at 1.5 Tesla). The 180° opposed-phase can be easily avoided by some small adjustments in the receiver bandwidth and/or the frequency encoding steps. It is interesting to note that when the water and fat are of the opposed phase, the phase correction method of the present invention still performs well even though the water and fat separation using Eqs. [2-3] is not possible. As an alternative and similar to the tissue segmentation using phase-sensitive inversion recovery images, a water-dominant image and a fat-dominant image may be obtained as the image with only the positive pixel values and the image with only the negative pixel values, respectively. Ma, J., *Multislice and Multicoil Phase Sensitive Inversion Recovery Imaging*, Magn Reson Med, 2005, 53:904-910; Ma, J., *Phase-Sensitive IR Imaging and Its Application For Tissue Segmentation*, In: Proceedings of the Seventh Annual Scientific Meeting of the International Society of Magnetic Resonance in Medicine, Philadelphia, Pa., 1999, p 1652. FIG. 9a displays an image of the same phantom as in FIG. 3 but collected at a TE of 2.42 ms. Because of the nearly opposed-phase angle of 179.2°, the fat-suppressed image and the water-suppressed image according to Eqs. [2-3] show poor water and fat separation (FIGS. 9b and 9c). In contrast, satisfactory results were achieved in the water-dominant image (FIG. 9d) and the fat-dominant image (FIG. 9e) after the phase correction of the same image.

Example 5

Silicone/Water/Fat Phantom Images

Figure 10:
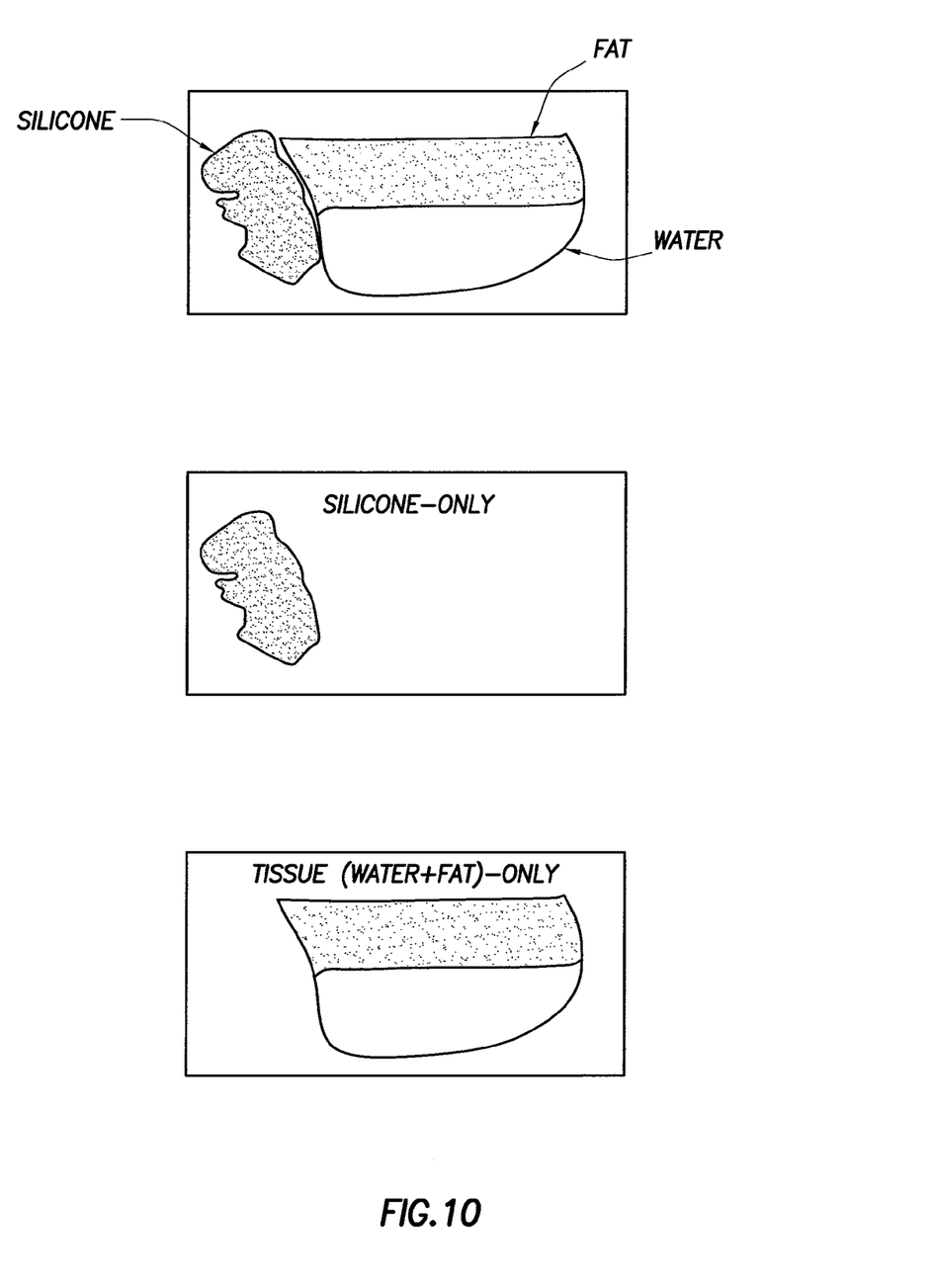
FIG. 10 shows the magnitude image (top), the silicone-only image (bottom left), and the water+fat image of a phantom containing three distinct chemical species (water, fat, and silicone).

The data for the images in FIGS. 10a-10c were collected on a 1.5 Tesla MR scanner using an eight channel head RF coil and of a phantom containing water, fat, and a silicone implant. A fast 3D spoiled gradient echo sequence was used for data collection. The scan parameters were FOV (field-of-view)=20×15 cm, acquisition matrix=256×160, slice thickness=4 mm, total number of slices=32. The echo time (TE) was set so that water and fat are substantially in-phase. The total scan time for the whole 3D volume was 25 seconds.

FIG. 10a (top image) was generated using the conventional magnitude reconstruction and represents one of the 32 slices of the 3D acquisition. It contains all the chemical species in the phantom (water, fat, and silicone). FIG. 10b (bottom left) represents the silicone-only image and FIG. 10c (bottom right) represents the tissue-only image (which contains water and fat) for the same slice as for the top image. FIGS. 10b and 10c are generated according to the phase correction method disclosed herein. Silicone leakage from an implant can be easily visualized and detected on a silicone-only image as illustrated by FIG. 10b.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A method comprising:
acquiring a plurality of magnetic resonance image ("MRI") data signals utilizing a single echo data acquisition, wherein the echo time can be flexible;
forming a complex image corresponding to the single echo acquisition said image comprising a plurality of pixels, wherein a pixel value comprises amplitude and phase information;
forming two complex images $DX_{mn}$ and $DY_{mn}$ using the complex image, wherein each of the pixels in $DX_{mn}$ and $DY_{mn}$ is given by the phase difference between two neighboring pixels along the x- and y-directions, respectively;
selecting an initial seed pixel from the plurality of pixels and placing the initial seed pixel onto one of a plurality of pixel stacks wherein the initial seed pixel may have the smallest $DX_{mn}$ and $DY_{mn}$ value of any of the neighbor pixels and is adjacent to at least four neighbor pixels;
performing a region-growing algorithm for phase correction in the complex image, wherein the region-growing algorithm places each neighbor pixel onto a pixel stack as determined by $DX_{mn}$ and $DY_{mn}$ value of the pixel;
determining the phase-corrected value of a pixel during the region growing by using a reference based on both the amplitude and the phase information of pixels that have been phase-corrected and that lie within the neighborhood of the pixel under consideration;
separating chemical species within the image; and
obtaining one or more images containing one or more of the separated chemical species.

2. The method of claim 1 wherein the step of acquiring the plurality of MRI data signals comprises acquiring data from one or more of multiple slices and multiple receiver coils.

3. The method of claim 1 wherein the step of acquiring the plurality of MRI data signals comprises using two-dimensional or three dimensional gradient echo pulse sequences.

4. The method of claim 3 further comprising selecting an echo time such that a phase shift is obtained between chemical species present in the imaging volume.

5. The method of claim 3 further comprising selecting an echo time such that two or more chemical species are substantially in-phase when three or more chemical species are present within the imaging volume.

6. The method of claim 1 wherein the step of acquiring the plurality of MRI data signals comprises using two-dimensional or three dimensional spin echo or fast spin echo pulse sequences.

7. The method of claim 6 further comprising selecting an echo shift from spin echo times such that a phase shift is obtained between chemical species present in the imaging volume.

8. The method of claim 6 further comprising selecting an echo shift from spin echo times such that two or more chemical species are substantially in-phase when three or more chemical species are present within the imaging volume.

9. The method of claim 1 wherein the step of acquiring the plurality of MRI data signals comprises performing one or more of a pulse sequence and a partially parallel imaging technique.

10. The method of claim 1 wherein the step of performing a region-growing algorithm comprises:

calculating a phase gradient along a first axis between neighboring pixels of the complex image;
calculating a phase gradient along a second axis between neighboring pixels of the complex image;
using the phase gradients and a plurality of pixel stacks to determine and guide the sequence of the region growing; and
using both the amplitude and the phase information of pixels that have been phase-corrected and that lie within the neighborhood of a pixel under consideration to guide the determination of a phase corrected value for the pixel under consideration.

11. The method of claim 1 further comprising:
performing the region growing algorithm by assuming that an initial pixel is dominated by a first chemical species;
calculating a first absolute angular difference between a first actual phase error vector of a pixel and a first projected phase error of the pixel;
calculating a first total absolute angular difference by summing the first absolute angular differences over the entire complex image;
performing the region-growing algorithm by assuming that the initial pixel is dominated by a second chemical species;
calculating a second absolute angular difference between a second actual phase error vector of a pixel and a second projected phase error of the pixel;
calculating a second total absolute angular difference by summing the second absolute angular differences over the entire complex image; and
comparing the first and second total absolute angular differences to determine whether the initial pixel is dominated by the first or second chemical species.

12. The method of claim 1 wherein:
the plurality of MRI data signals are acquired on a plurality of receiver coils; and the step of obtaining one or more images containing one or more of the separated chemical species comprises:
calculating and comparing one or more coil-coil correlation indices; and
combining MRI data signals from the plurality of receiver coils.

13. The method of claim 1 wherein the chemical species comprise water and fat.

14. The method of claim 13 wherein the step of obtaining one or more images containing one or more of the separated chemical species comprises obtaining one or more of a fat-suppressed image and a water-suppressed image.

15. The method of claim 1 wherein the chemical species comprise water, fat, and silicone.

16. The method of claim 15 wherein the step of obtaining one or more images containing one or more of the separated chemical species comprises obtaining one or more of a silicone-only image and a fat-and-water-only image.

17. The method of claim 1 wherein the echo time is selectable by an operator.

18. The method of claim 17 wherein: the chemical species comprise water, fat, and silicone; and the echo time is selected such that the MRI data signals from the water and fat are substantially in phase with each other and the MRI data signals from the silicone are substantially out of phase from the water and fat signals.

19. The method of claim 18 wherein the step of obtaining one or more images containing one or more of the separated chemical species comprises obtaining one or more of a silicone-only image and a fat-and-water-only image.

20. A system comprising:

a magnetic resonance imaging scanner for providing a plurality of data signals following a scan;

an apparatus adapted to provide a pulse sequence to collect the data signals;

a controller coupled to the magnetic resonance imaging scanner; and an output device coupled to the controller, the output device adapted to display the separate images; wherein the controller receives the data signals, implements a single-point Dixon technique with selectable phase shifts between different chemical species to produce a complex image from the data signals, performs a region-growing algorithm for correcting phase errors in the complex image using the phase gradients and a plurality of pixel stacks to guide the region growing, wherein the region-growing algorithm places each neighbor pixel onto a pixel stack as determined by $DX_{mn}$ and $DY_{mn}$ of the pixel, and thereby performs separation of different chemical species within the image and obtains separate images containing one or more of the chemical species, and the separate images are displayed on the output device.

\* \* \* \* \*